(12) United States Patent
Naughton et al.

(10) Patent No.: US 8,128,924 B2
(45) Date of Patent: Mar. 6, 2012

(54) METHODS FOR USING A THREE-DIMENSIONAL STROMAL TISSUE TO PROMOTE ANGIOGENESIS

(75) Inventors: Gail K. Naughton, Del Mar, CA (US); Jonathan Noel Mansbridge, La Jolla, CA (US); Robert Emmett Pinney, Poway, CA (US); Joan Zeltinger, San Diego, CA (US)

(73) Assignee: Theregen, Inc., San Francisco, CA (US)

( * ) Notice: Subject to any disclaimer, the term of this patent is extended or adjusted under 35 U.S.C. 154(b) by 0 days.

(21) Appl. No.: 12/420,716

(22) Filed: Apr. 8, 2009

(65) Prior Publication Data

US 2009/0269316 A1    Oct. 29, 2009

Related U.S. Application Data

(63) Continuation of application No. 10/851,938, filed on May 21, 2004, now abandoned, which is a continuation of application No. 09/411,585, filed on Oct. 1, 1999, now abandoned.

(60) Provisional application No. 60/128,838, filed on Apr. 12, 1999.

(51) Int. Cl.
*C12N 5/00* (2006.01)

(52) U.S. Cl. ............... 424/93.7; 424/422; 424/423

(58) Field of Classification Search .................. None
See application file for complete search history.

(56) References Cited

U.S. PATENT DOCUMENTS

| | | | |
|---|---|---|---|
| 4,359,049 A | 11/1982 | Redl et al. | |
| 4,414,976 A | 11/1983 | Schwarz et al. | |
| 4,627,879 A | 12/1986 | Rose et al. | |
| 4,721,096 A | 1/1988 | Naughton et al. | |
| 4,874,368 A | 10/1989 | Miller et al. | |
| 4,963,489 A * | 10/1990 | Naughton et al. | 435/1.1 |
| 5,032,508 A | 7/1991 | Naughton et al. | |
| 5,266,480 A | 11/1993 | Naughton et al. | |
| 5,290,552 A | 3/1994 | Sierra et al. | |
| 5,318,524 A | 6/1994 | Morse et al. | |
| 5,368,563 A | 11/1994 | Lonneman et al. | |
| 5,387,236 A | 2/1995 | Noishiki et al. | |
| 5,478,739 A * | 12/1995 | Slivka et al. | 435/399 |
| 5,512,475 A | 4/1996 | Naughton et al. | |
| 5,605,541 A | 2/1997 | Holm | |
| 5,643,192 A | 7/1997 | Hirsh et al. | |
| 5,709,854 A | 1/1998 | Griffith-Cima et al. | |
| 5,759,171 A | 6/1998 | Coelho et al. | |
| 5,763,267 A | 6/1998 | Kurjan et al. | |
| 5,785,964 A | 7/1998 | Naughton et al. | |
| 5,830,708 A | 11/1998 | Naughton et al. | |
| 5,843,766 A | 12/1998 | Applegate et al. | |
| 5,962,325 A | 10/1999 | Naughton et al. | |
| 6,099,832 A * | 8/2000 | Mickle et al. | 424/93.21 |
| 6,140,039 A | 10/2000 | Naughton et al. | |
| 6,284,284 B1 | 9/2001 | Naughton | |
| 6,372,494 B1 | 4/2002 | Naughton et al. | |
| 6,528,080 B2 | 3/2003 | Dunn et al. | |
| 6,730,016 B1 | 5/2004 | Cox et al. | |
| 2001/0014475 A1 | 8/2001 | Frondoza et al. | |
| 2002/0025308 A1 | 2/2002 | Costantino et al. | |
| 2003/0003089 A1 | 1/2003 | Akins, Jr. | |
| 2003/0007954 A1 | 1/2003 | Naughton et al. | |
| 2003/0068817 A1 | 4/2003 | Gazit et al. | |
| 2003/0211088 A1 | 11/2003 | Field | |
| 2004/0117033 A1 | 6/2004 | Frondoza et al. | |
| 2004/0219134 A1 | 11/2004 | Naughton et al. | |
| 2006/0115460 A1 | 6/2006 | Naughton | |
| 2006/0140916 A1 | 6/2006 | Siani-Rose et al. | |
| 2006/0154365 A1 | 7/2006 | Ratcliffe et al. | |
| 2006/0292125 A1 | 12/2006 | Kellar et al. | |

FOREIGN PATENT DOCUMENTS

| | | |
|---|---|---|
| EP | 0385506 | 9/1990 |
| EP | 1367119 | 12/2003 |
| WO | WO 94/22505 | 10/1994 |
| WO | WO 95/25547 | 9/1995 |
| WO | WO 96/08213 | 3/1996 |
| WO | WO 99/00152 | 1/1999 |
| WO | WO 99/52573 | 10/1999 |
| WO | WO 00/34442 | 6/2000 |
| WO | WO 2004/058952 | 7/2004 |
| WO | WO 2004/074457 | 9/2004 |

OTHER PUBLICATIONS

Jiang et al, International Journal of Molecular Medicine, 1998, vol. 2, pp. 203-210.*
Weihrauch et al, Molecular and Cellular Biochemistry, 1995, vol. 147, pp. 13-19.*
Asahara et al, Science, 1997, vol. 275, pp. 964-967.*
Edelberg et al., "PDGF Mediates Cardiac Microvascular Communication." J. Clin. Invest., 102(4):837-843 (1998).
Edgington, S. M., "Angiogenic and Angiostatic Drugs: Reshaping Biotech's Future." Bio/Technology, 10:981-985 (1992).

(Continued)

*Primary Examiner* — Allison Ford
(74) *Attorney, Agent, or Firm* — Dechert LLP

(57) ABSTRACT

The present invention relates to a method for promoting blood vessel formation in tissues and organs. In particular, the method relates to implantation or attachment of an engineered three-dimensional stromal tissue to promote endothelialization and angiogenesis in the heart and related tissues. The three-dimensional stromal tissue of the present invention may be used in a variety of applications including, but not limited to, promoting repair of and regeneration of damaged cardiac muscle, promoting vascularization and healing during cardiac surgery, promoting blood vessel formation at anastomosis sites, and promoting vascularization and repair of damaged skeletal muscle, smooth muscle or connective tissue.

12 Claims, 9 Drawing Sheets

OTHER PUBLICATIONS

Figure 1A:
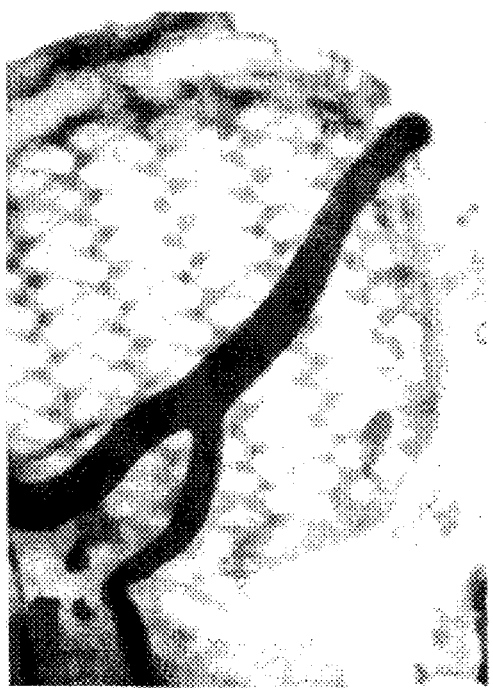

Engler, D. A., "Use of Vascular Endothelial Growth Factor for Therapeutic Angiogenesis." Circulation, 94:1496-1498 (1996).

Gentzkow et al., "Improved Healing of Diabetic Foot Ulcers After Grafting with a Living Human Dermal Replacement." Wounds: A Compendium of Clinical Research and Practice, 11(3):77-84 (1999).

Hudlicka et al., "Angiogenesis in Skeletal and Cardiac Muscle." Physiological Reviews, 72(2):369-417 (1992).

Kellar et al., "Scaffold-Based Three-Dimensional Human Fibroblast Culture Provides a Structural Matrix that Supports Angiogenesis in Infarcted Heart Tissue." Circulation, 104:2063-2068 (2001).

Kuzuya et al., "Reorganization of Endothelial Cord-Like Structures on Basement Membrane Complex (Matrigel): Involvement of Transforming Growth Factor 1." Journal of Cellular Physiology, 161:267-276 (1994).

Li et al., "VEGF, flk-1, and flt-1 Expression in a Rat Myocardial Infarction Model of Angiogenesis." Am. J. Physiol., 270(5), Pt. 2:H1803-H1811 (1996).

Losordo et al., "Gene Therapy for Myocardial Angiogenesis: Initial Clinical Results with Direct Mycardial Injection of phVEGF 165 as Sole Therapy for Myocardial Ischemia." Circulation, 98(25):2800-2804 (1998).

Mansbridge et al., "Three Dimensional Fibroblast Culture Implant for the Treatment of Diabetic Foot Ulcer: Metabolic Activity and Therapeutic Range." Tissue Engineering, 4(4):403-414 (1998).

Mansbridge, J., "Skin Substitutes to Enhance Would Healing." Exp. Opin. Invest. Drugs, 7(5):803-809 (1998).

Mansbridge, J., "Tissue-Engineering Skin Substitutes." Exp. Opin. Invest. Drugs, 8(7):957-962 (1999).

Medical Industry Today, MDI Online, Firm to Redirect Study on Vascular Endothelial Growth Factor, Companies: Genenttech, Inc., Date: Feb. 19, 1999, Category: Drug and Biotechnology News (1999).

Miyataka et al., "Basic Fibroblast Growth Factor Increased Regional Myocardial Blood Flow and Limited Infarct Size of Acutely Infarcted Myocardium in Dogs." Angiology, 49(5):381-390 (1998).

Montesano, R., "Regulation of Angiogenesis in vitro." European Journal of Clinical Investigation, 22:504-515 (1992).

Montesano et al., "Practice Induction of Angiogenesis in vitro by Swiss 3T3 Fibroblasts." Journal of Cell Science, 105:1013 (1993).

Mulder et al., "The Role of Tissue Engineering in Wound Care." Journal of Wound Care, 8(1):21-24 (1999).

Nehls et al., "Contact-Dependent Inhibition of Angiogenesis by Cardiac Fibroblasts in Three-Dimensional Fibrin Gels in vitro: Implications for Microvascular Network Remodeling and Coronary Collateral Formation." Cell Tissue Res., 293(3):479-488 (1998).

Newton, D. J., "Blood Flow Changes in Diabetic Foot Ulcers Treated with Dermagraft." 3rd Joint Meeting of the European Tissue Repair Society and The Wound Healing Society, Aug. 24-28, 1999.

Pinney, E., "Angiogenic Properties of Dermagraft, a Human Dermal Implant Use to Treat Diabetic Foot Ulcers." Keystone Abstract (1998).

Senger, D. R., "Molecular Framework for Angiogenesis, A Complex Web of Interactions Between Extravasated Plasma Proteins and Endothelial Cell Proteins Induced by Angiogenic Cytokines." American Journal of Pathology, 149(1):1-7 (1996).

Steed, D. L., "Debridement." The American Journal of Surgery Supplement, 187:71S-74S (2004).

Steed, et al., "Clinical Evaluation of Recombinant Human Platlet-Derived Growth Factor for the Treatment of Lower Extremity Diabetic Ulcers." Journal of Vascular Surgery, 21:71-81 (1995).

Uchida et al., "Angiogenic Therapy of Acute Myocardial Infarction by Intrapericardial Infection of Basic Fibroblast Growth Factor and Heparin Sulfate: An Experimental Study." Am. Heart J., 130(6):1182-1188 (1995).

Voyta et al., "Gene Therapy for Myocardial Angiogenesis, Initial Clinical Results with Direct Myocardial Injection of ph VEGF Sole Therapy for Myocardial Ischemia," The Journal of Cell Biology, 99:2034-2040 (1984).

Voyta et al., "Identification and Isolation of Endothelial Cells Based on Their Increased Uptake of Acetylated-Low Density Lipoprotein." The Journal of Cell Biology, 99:2034-2040 (1984).

Ware et al., "Angiogenesis in ischemic heart disease." Nature Medicine, vol. 3, No. 2, pp. 158-164 (1997).

Watanabe et al., "Effect of Basic Fibroblast Growth Factor on Angiogenesis in the Infarcted Porcine Heart." Basic Res. Cardiol., 93(1):30-37 (1998).

Yates, K. E., "Demineralized Bone Alters Expression of WNT Network Components During Chondroinduction of Post-Natal Fibroblasts." OsteoArthritis and Cartilage, 12(6):497-505 (2004).

Ziegler et al., "Co-culture of endothelial cells and smooth muscles in a flow environment: an improved culture model of the vascular wall?" Cells and Materials, U.S. Scanning Microscopy International, Chicago, 5(2):115-124 (1995).

European Search Report from EP 07003001.0 dated Apr. 19, 2007.

PCT International Search Report from PCT/US00/09848 dated Sep. 1, 2000.

PCT International Search Report from PCT/US05/030912 dated Jun. 21, 2006.

PCT International Search Report from PCT/US05/031210 dated Jul. 5, 2006.

PCT International Search Report from PCT/US05/042698 dated Jun. 12, 2006.

Non-Final Office Action in U.S. Appl. No. 11/285,932 mailed Oct. 19, 2007.

Non-Final Office Action in U.S. Appl. No. 11/216,507 mailed Jun. 13, 2006.

Final Office Action in U.S. Appl. No. 11/216,507 mailed Mar. 8, 2007.

Non-Final Office Action in U.S. Appl. No. 11/216,574 mailed Dec. 19, 2006.

Final Office Action in U.S. Appl. No. 11/216,574 mailed Sep. 11, 2007.

* cited by examiner

US 8,128,924 B2

METHODS FOR USING A THREE-DIMENSIONAL STROMAL TISSUE TO PROMOTE ANGIOGENESIS

This application is a continuation of Ser. No. 10/851,938, filed May 21, 2004, now abandoned which is a continuation of Ser. No. 09/411,585, filed Oct. 1, 1999 now abandoned which claims priority to provisional application No. 60/128,838, filed Apr. 12, 1999, each of which is incorporated herein by reference.

1. INTRODUCTION

The present invention relates to a method for promoting angiogenesis in organs and tissues. In particular, the method relates to implantation or attachment of a three-dimensional stromal tissue to promote endothelialization and vascularization in the heart and related tissues.

2. BACKGROUND OF THE INVENTION

Coronary heart disease is the single leading cause of death in America today (American Heart Association's "1999 Heart and Stroke Statistical Update"). This disease, as with various other cardiovascular disorders, is characterized by the narrowing of arteries and inadequate blood flow to critical tissues.

Currently used clinical methods for improving blood flow in a diseased or otherwise damaged heart involve invasive surgical techniques such as coronary by-pass surgery, angioplasty, and endarterectomy. Such procedures naturally involve high-degrees of inherent risk during and after surgery, and often only provide a temporary remedy to cardiac ischemia.

In an effort to improve the prognosis of surgical procedures on the heart, physicians and researchers have attempted to use pumps to assist blood flow during surgery. However, such pumps only act as temporary assist devices during surgery, they cannot be used as a form of treatment for the cardiac condition.

An alternative, or at least a compliment, to coronary by-pass and other surgical procedures to improve blood flow in the heart is to induce tissues in the heart to form new blood vessels. In that regard, angiogenic compounds such as vascular endothelial growth factor (VEGF), have been used in an effort to facilitate the formation of new blood vessels. One approach to using VEGF to promote blood vessel formation in heart tissue has been to inject the protein directly into a patient's body. However, such attempts have been largely unsuccessful.

Recently, a gene-therapy approach was used to deliver VEGF by injection of retroviral vectors that targeted heart tissue and resulted in VEGF production (Losordo et al., 1998, Circulation 98:2800-2804). This in situ method improved blood flow and subjective symptoms in patients, suggesting that local delivery of a growth factor such as VEGF to promote angiogenesis in heart tissues may be of therapeutic value in the treatment of certain heart conditions. However, such gene therapy techniques utilizing retroviral vectors present certain inherent risks and safety concerns. In addition, gene therapy-type approaches present a number of unresolved, problematic technical hurdles such as low transfection levels for recipient cells, construct instability and long-term expression of the desired gene product from the transfected cells.

3. SUMMARY OF THE INVENTION

The present invention relates to a method for promoting blood vessel formation in tissues and organs. In particular, the method relates to implantation or attachment of a three-dimensional stromal tissue to promote endothelialization and angiogenesis in the heart and related tissues.

The invention has a variety of applications including, but not limited to, promoting repair of and regeneration of damaged cardiac muscle, promoting vascularization and healing during cardiac surgery (e.g. by-pass surgery or heart valve replacement), promoting blood vessel formation at anastomosis sites, and promoting vascularization and healing of ischemic or otherwise damaged tissues such as skeletal muscle, smooth muscle, brain tissue or connective tissue.

The invention is based in part on the discovery that three-dimensional stromal tissue constructs, when implanted in the wound bed of patients with diabetic foot ulcers, are capable of inducing rapid endothelialization and vascularization, resulting in new capillary formation and reduced inflammation in the wounded tissue.

The three-dimensional stromal tissue implants secrete a variety of growth factors critical to tissue regeneration and angiogenesis, most notably vascular endothelial growth factor, or VEGF (Table II). The invention encompasses the application of the three-dimensional stromal tissue to damaged tissues, such as damaged cardiac muscle, to induce a new local blood supply to the area and support rapid tissue remodeling.

A three-dimensional stromal tissue implant may also be used to promote formation of a "natural" carotid by-pass to assist in, or obviate the need for, carotid endarterectomy surgery (which can often result in stroke due to downstream flow of particles dislodged during the procedure).

4. BRIEF DESCRIPTION OF THE DRAWINGS

Figure 1B:
Figure 1C:
Figure 1D:
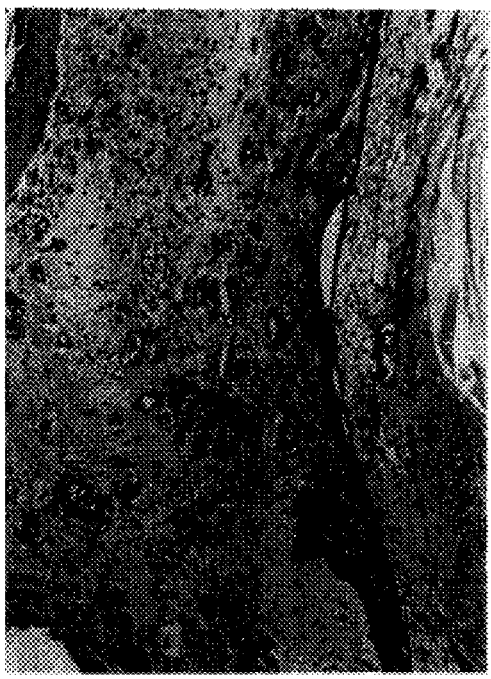

FIG. 1A-1D Photomicrographs showing engineered stromal tissue-stimulated angiogenesis in a chick chorioallantoic membrane (CAM). FIGS. 1A and 1B show macroscopic view, while FIGS. 1C and 1D show histology. FIG. 1A shows scaffold alone, FIG. 1C shows non-viable, and FIGS. 1B and 1D show Three-dimensional stromal tissue treated membrane.

Figure 2:
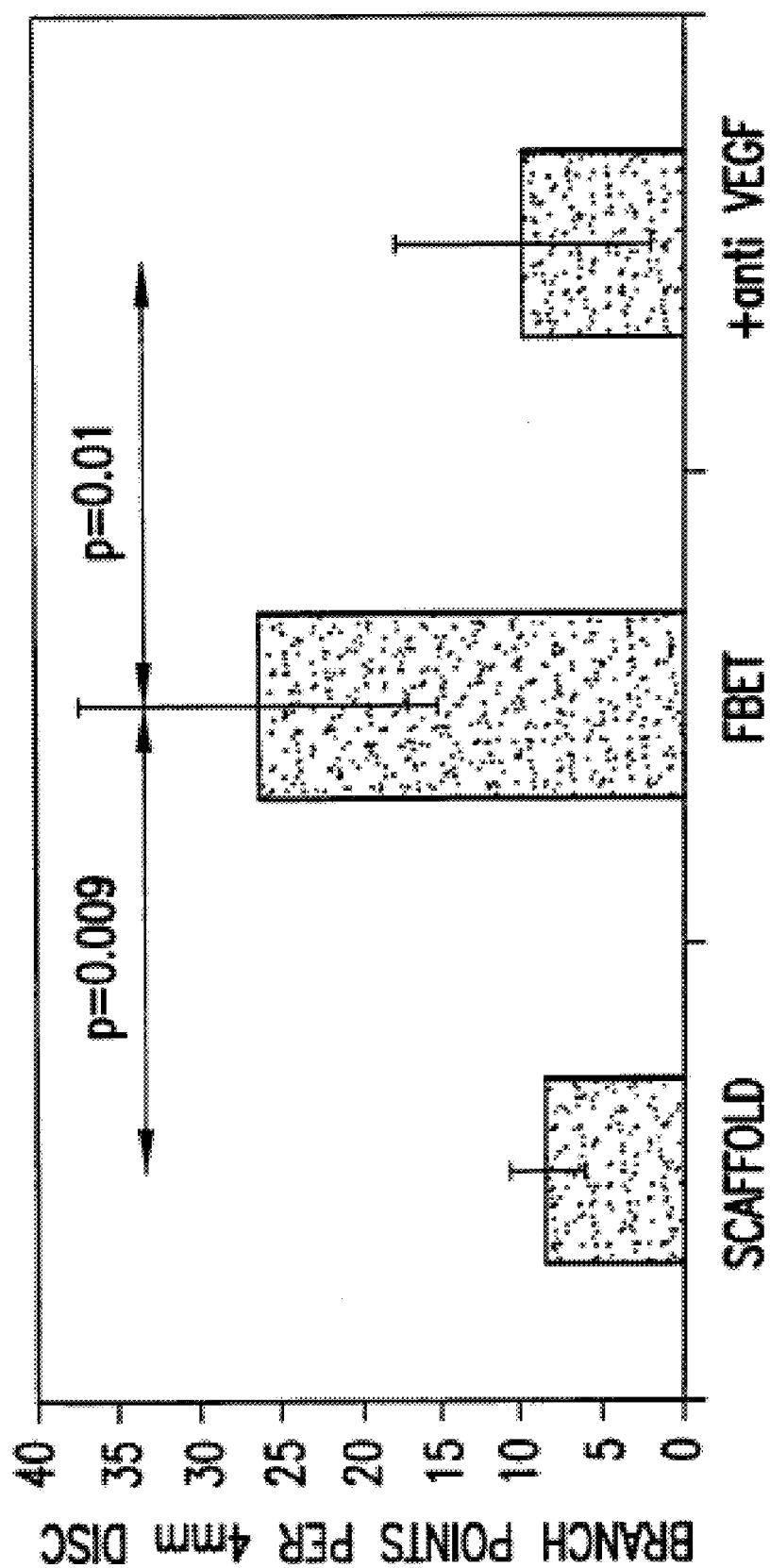

FIG. 2 Bar graph depicting the effect of engineered stromal tissue on capillary blood vessel formation in a chick chorioallantoic membrane. Bars represent 95% confidence intervals.

Figure 3:
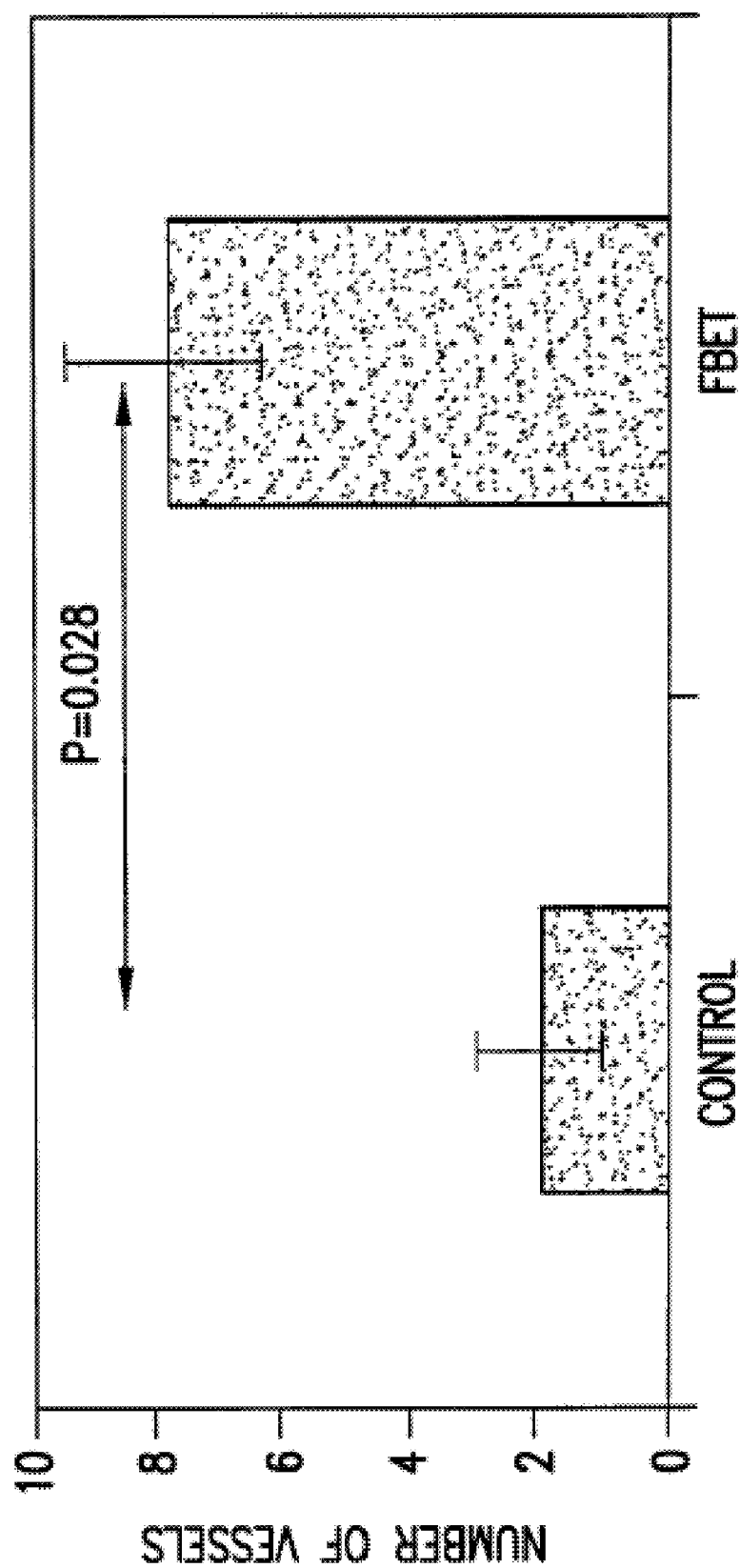

FIG. 3 Bar graph depicting blood vessel formation stimulated by engineered stromal tissue in a rat aortic ring assay.

Figure 4:
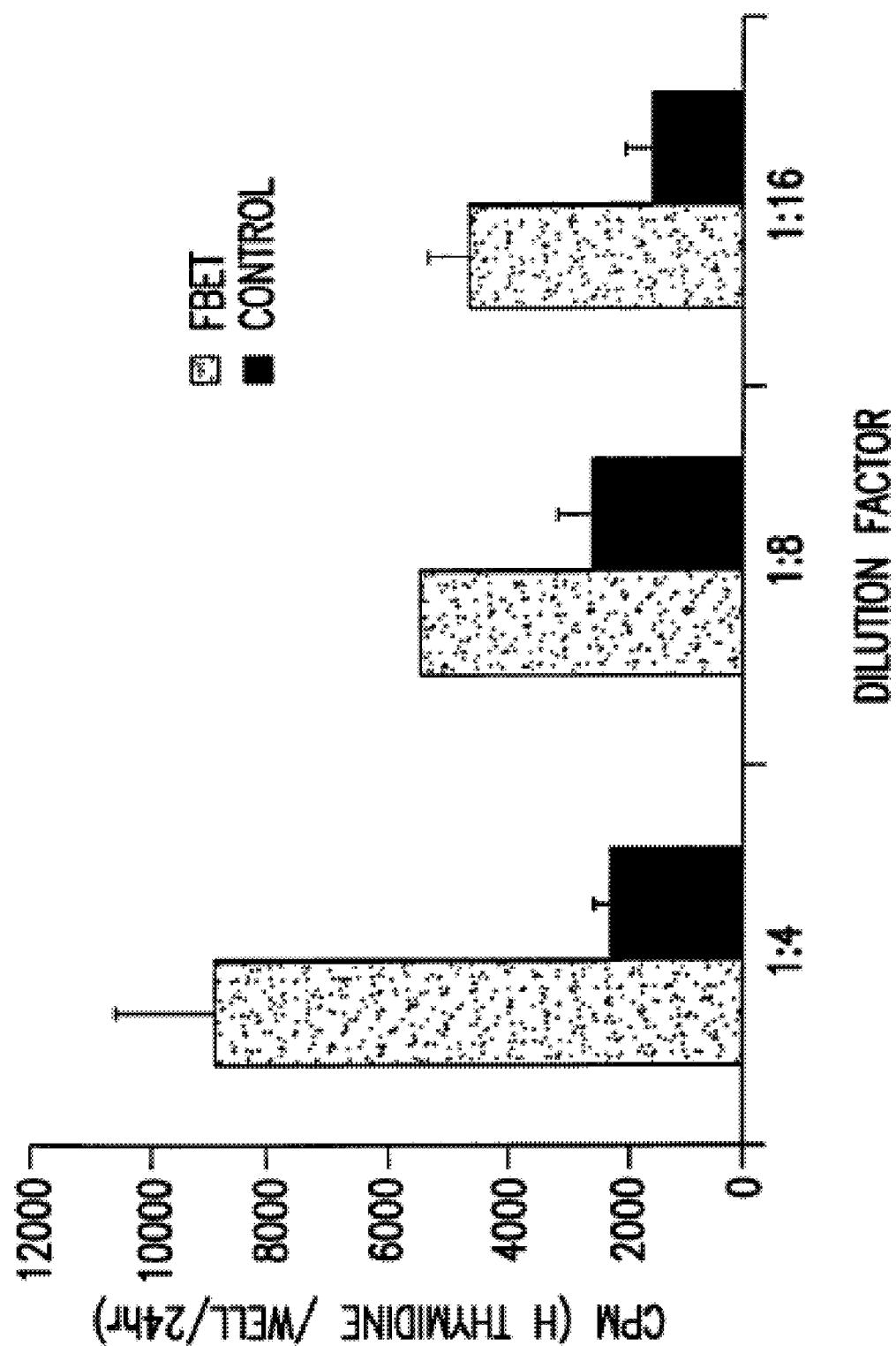

FIG. 4 Bar graph depicting proliferation of human umbilical vein endothelial cell (HUVEC) in vitro following stimulation by engineered stromal tissue conditioned medium.

Figure 5:
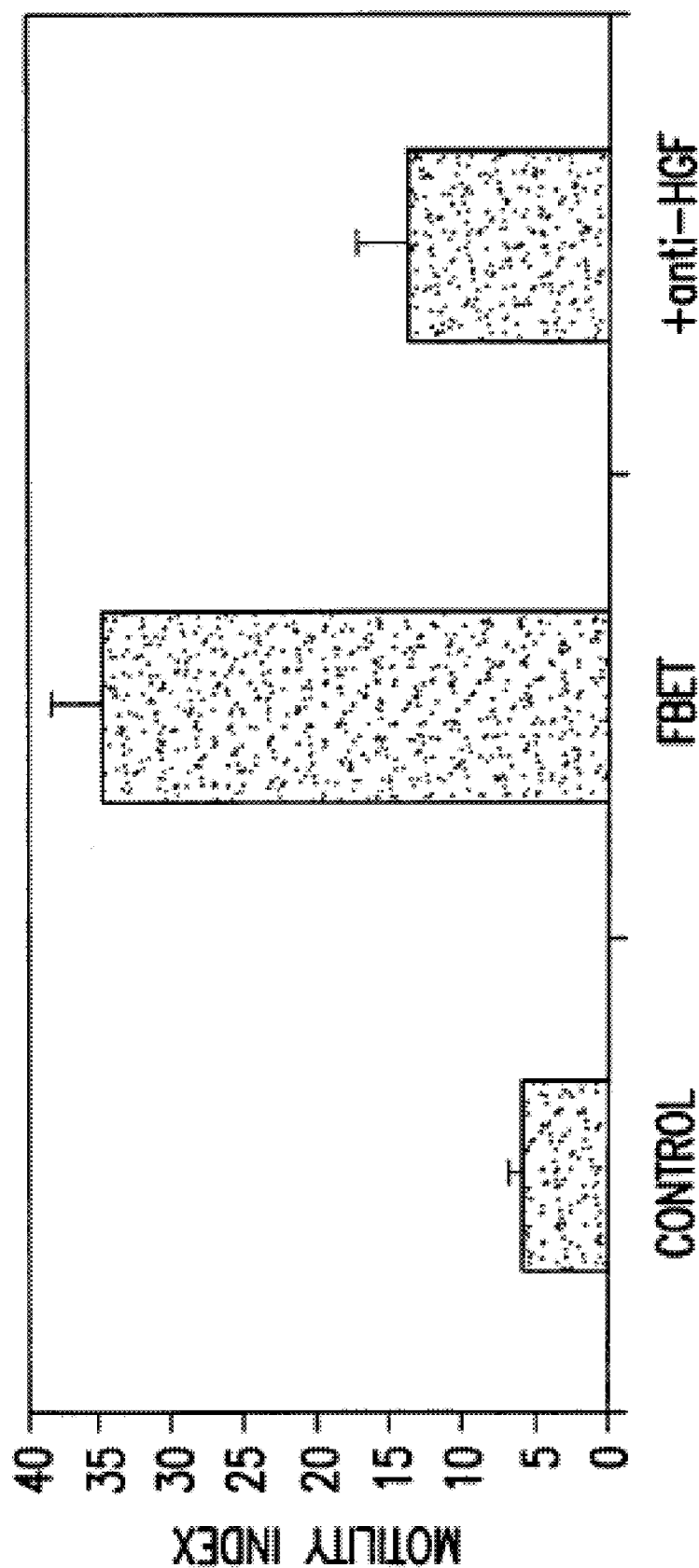

FIG. 5 Bar graph depicting stimulation of endothelial cell motility by engineered stromal tissue.

Figure 6:
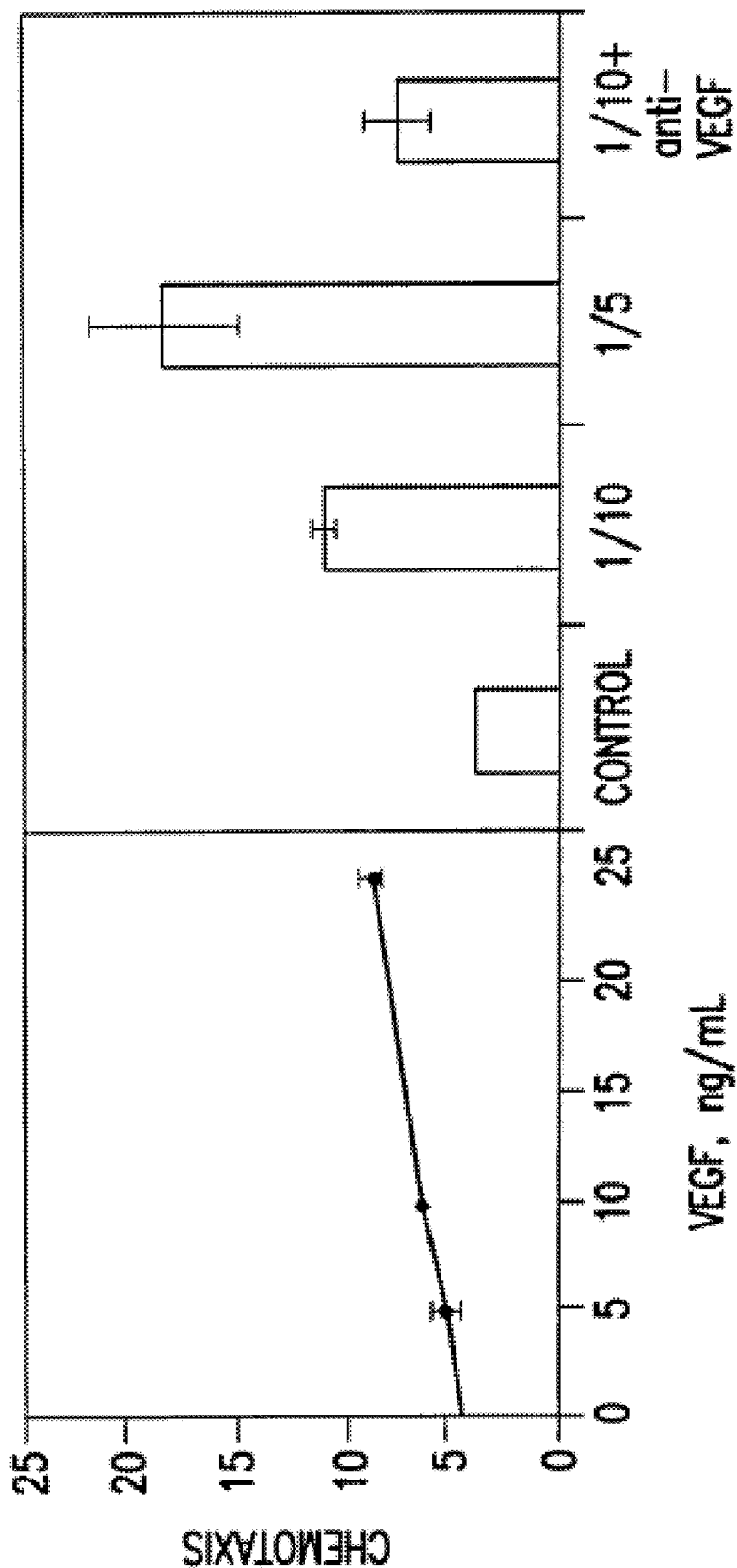

FIG. 6 Graphs depicting stimulation of endothelial cell chemotaxis by engineered stromal tissue (left side shows standard curve using purified VEGF at indicated concentrations).

Figure 7:
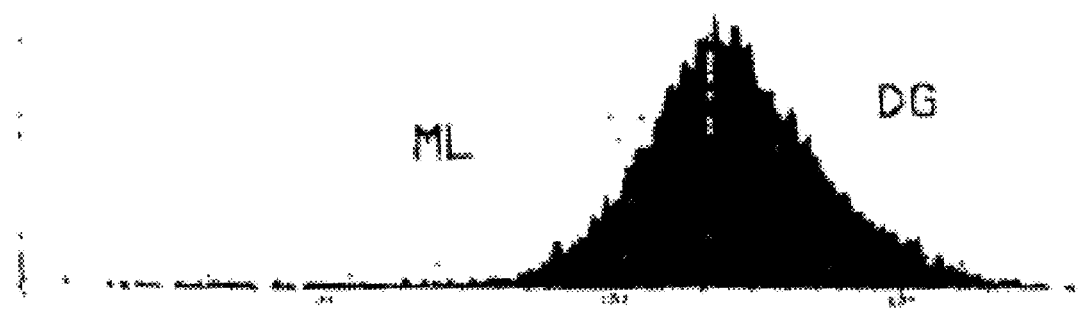

FIG. 7 Flow cytometry result depicting induction of integrin $\alpha_v\beta_1$ expression on endothelial cells by engineered stromal tissue.

Figure 8A:
Figure 8B:
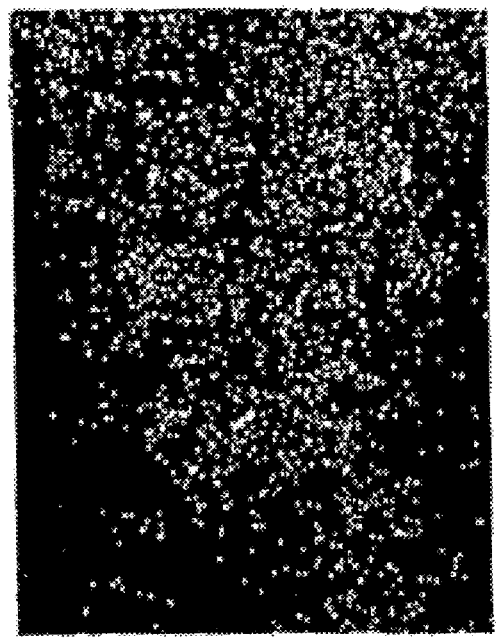

FIGS. 8A and 8B Photomicrographs depicting inhibition of endothelial cell apoptosis cultured on "MATRIGEL" in the presence of engineered stromal tissue. The cells were stained with low density lipoprotein and sytox, which stained nuclei of apoptotic cells.

Figure 9A:
Figure 9B:
Figure 9C:
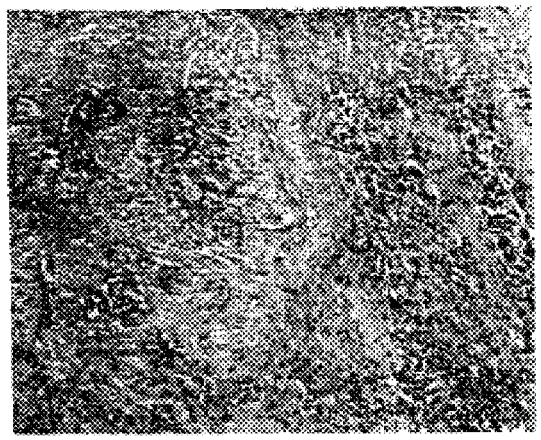
Figure 9D:
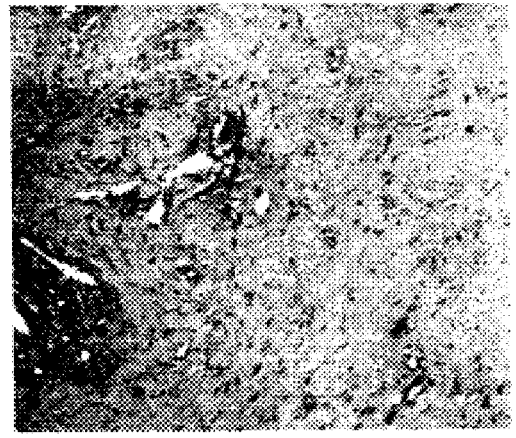

FIG. 9A-9D Photomicrographs of a human diabetic ulcer showing engineered stromal tissue-stimulated vascularization of the wound bed, remodeling of the tissue, and reduction in inflamation. FIGS. 9A and 9C show the wound bed before treatment, while FIGS. 9B and 9D show the wound bed after treatment.

5. DETAILED DESCRIPTION OF THE INVENTION

The present invention relates to a method for promoting blood vessel formation in tissues and organs of a subject, particularly a human subject. In particular, the method relates to implantation or attachment of an engineered three-dimensional stromal tissue to promote endothelialization and angiogenesis in the heart and related tissues.

The invention has a variety of applications including, but not limited to, promoting repair of and regeneration of damaged cardiac muscle, promoting vascularization and healing during cardiac surgery (e.g. by-pass surgery or heart valve replacement), promoting blood vessel formation at anastomosis sites, and promoting vascularization and repair of damaged skeletal muscle, connective tissue, or other tissues.

The invention is based, in part, on the discovery that three-dimensional stromal tissues, when implanted in the wound bed of patients with diabetic foot ulcers, are capable of inducing endothelialization and vascularization, resulting in new capillary formation and reduced inflammation in the wounded tissue.

The three-dimensional stromal tissue comprises stromal cells grown on a three-dimensional substrate or framework composed of a biocompatible, non-living material formed into a three-dimensional structure having interstitial spaces bridged by the stromal cells. The stromal cells preferably comprise fibroblasts with or without additional cells and/or elements described more fully herein below. In particular, the additional cells may comprise smooth muscle cells, cardiac muscle cells, endothelial cells or skeletal muscle cells. The fibroblasts and/or other cells may be fetal or adult in origin, and may be derived from convenient sources such as skin, cardiac muscle, smooth muscle, skeletal muscle, liver, pancreas, brain etc. Such tissues and or organs can be obtained by appropriate biopsy or upon autopsy. In fact, cadaver organs may be used to provide a generous supply of stromal cells and elements.

It is to be understood that one skilled in the art can control the angiogenic activity of a stromal tissue culture by incorporating cells that release different levels of angiogenic factors. For example, vascular smooth muscle cells, preferably aortic smooth muscle cells, are known to produce substantially more VEGF than human dermal fibroblasts. Therefore, by utilizing aortic smooth muscle cells instead of or in addition to fibroblasts, one can culture three-dimensional stromal tissues with enhanced angiogenic activity.

In an alternative embodiment of the invention, a three-dimensional stromal tissue implant that is genetically engineered to have improved properties for inducing angiogenesis may be used to promote formation of new blood vessels in the heart or other tissues.

In another embodiment, the invention encompasses a method of treatment of eschemic damage to heart, brain, visceral organs or peripheral tissues. For example, and not by way of limitation, one embodiment of the invention entails attaching a three-dimensional stromal tissue to an ischemic region of a heart following myocardial infarction to promote vascularization of the heart and regeneration of damaged cardiac muscle cells. In the case of cerebral eschemia (e.g. resulting from a stroke and/or elevated intracranial pressure) the three dimensional stromal tissue implant may include fibroblasts, neural glial cells, neural stem cells, astrocytes, fibroblasts transfected with nerve growth factor, or a combination thereof. Such a stromal tissue implant is placed directly on the cerebral cortex or surgically implanted in the region of ischemia.

In yet another embodiment, the invention encompasses application of the three-dimensional stromal tissue to any tissue or organ to promote angiogenesis with the proviso that the organ or tissue is not a diabetic foot ulcer or a veinous ulcer.

5.1 Preparation of a Three-Dimensional Stromal Tissue

For the practice of the present invention, stromal cells are inoculated upon a three-dimensional framework, and grown to develop a stromal tissue. The three-dimensional support framework may be of any material and/or shape that: (a) allows cells to attach to it (or can be modified to allow cells to attach to it); and (b) allows cells to grow in more than one layer. Alternatively, a substantially two-dimensional sheet or membrane may be used to culture monolayers of cells.

A number of different materials may be used to form the framework, including but not limited to: nylon (polyamides), dacron (polyesters), polystyrene, polypropylene, polyacrylates, polyvinyl compounds (e.g., polyvinylchloride; PVC), polycarbonate, polytetrafluorethylene (PTFE; TEFLON), thermanox (TPX), nitrocellulose, cotton, polyglycolic acid (PGA), cat gut sutures, cellulose, gelatin, dextran, etc. Any of these materials may be woven into a mesh to form the three-dimensional framework. Certain materials, such as nylon, polystyrene, etc., are poor substrates for cellular attachment. When these materials are used as the three-dimensional support framework, it is advisable to pre-treat the framework prior to inoculation of stromal cells in order to enhance the attachment of stromal cells to the framework. For example, prior to inoculation with stromal cells, nylon screens could be treated with 0.1 M acetic acid, and incubated in polylysine, fetal bovine serum, and/or collagen to coat the nylon. Polystyrene could be similarly treated using sulfuric acid.

When the three-dimensional stromal tissue is to be implanted directly in vivo, it may be preferable to use biodegradable materials such as PGA, catgut suture material, collagen, polylactic acid, or hyaluronic acid. For example, these materials may be woven into a three-dimensional framework such as a collagen sponge or collagen gel. Where the cultures are to be maintained for long periods of time or cryopreserved, non-degradable materials such as nylon, dacron, polystyrene, polyacrylates, polyvinyls, teflons, cotton, etc. may be preferred. A convenient nylon mesh which could be used in accordance with the invention is Nitex, a nylon filtration mesh having an average pore size of 140 μm and an average nylon fiber diameter of 90 μm (#3-210/36, Tetko, Inc., N.Y.).

Stromal cells comprising fibroblasts, with or without other cells and elements described below, are inoculated onto the framework. These stromal cells may be derived from tissues or organs, such as skin, heart, blood vessels, skeletal muscle, liver, pancreas, brain etc., which can be obtained by biopsy (where appropriate) or upon autopsy. In fact, fibroblasts and other stromal cells can be obtained in quantity rather conveniently from any appropriate cadaver organ. As previously explained, fetal fibroblasts can be used to form a "generic" three-dimensional stromal tissue that will support the growth of a variety of different cells and/or tissues that come in contact with it. However, a "specific" stromal tissue may be prepared by inoculating the three-dimensional framework with stromal cells derived from the heart and/or from a particular individual who is later to receive the cells and/or tissues grown in culture in accordance with the three-dimensional culture of the invention.

Stromal cells may be readily isolated by disaggregating an appropriate organ or tissue. This may be readily accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include, but are not limited to, trypsin, chymotrypsin, collagenase, elastase, and/or hyaluronidase, DNase, pronase, dispase etc. Mechanical disruption can also be accomplished by a number of methods including, but not limited to, the use of grinders, blenders, sieves, homogenizers, pressure cells, or insonators to name but a few. For a review of tissue disaggregation techniques, see Freshney, Culture of Animal Cells. A Manual of Basic Technique, 2d Ed., A.R. Liss, Inc., New York, 1987, Ch. 9, pp. 107-126.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis and fluorescence-activated cell sorting. For a review of clonal selection and cell separation techniques, see Freshney, Culture of Animal Cells. A Manual of Basic Techniques, 2d Ed., A.R. Liss, Inc., New York, 1987, Ch. 11 and 12, pp. 137-168.

The isolation of stromal cells may, for example, be carried out as follows: fresh tissue samples are thoroughly washed and minced in Hanks balanced salt solution (HBSS) in order to remove serum. The minced tissue is incubated from 1-12 hours in a freshly prepared solution of a dissociating enzyme such as trypsin. After such incubation, the dissociated cells are suspended, pelleted by centrifugation and plated onto culture dishes. All stromal cells will attach before other cells, therefore, appropriate stromal cells can be selectively isolated and grown. The isolated stromal cells can then be grown to confluency, lifted from the confluent culture and inoculated onto the three-dimensional framework (U.S. Pat. No. 4,963,489; Naughton et al., 1987, J. Med. 18(3&4):219-250). Inoculation of the three-dimensional framework with a high concentration of stromal cells, e.g., approximately $10^6$ to $5 \times 10^7$ cells/ml, will result in the establishment of the three-dimensional stromal tissue in shorter periods of time.

In addition to fibroblasts, other cells may be added to form the three-dimensional stromal tissue required to support long term growth in culture. For example, other cells found in loose connective tissue may be inoculated onto the three-dimensional framework along with, or instead of, fibroblasts. Such cells include but are not limited to endothelial cells, pericytes, macrophages, monocytes, adipocytes, skeletal muscle cells, smooth muscle cells, cardiac muscle cells, etc. Such cells may be inoculated onto the three-dimensional framework in the absence of fibroblasts. These stromal cells may readily be derived from appropriate tissues or organs such as skin, heart, blood vessels, etc., using methods known in the art such as those discussed above. In a specific embodiment of the invention, fibroblasts are inoculated onto the framework.

It is to be understood that one skilled in the art can control the angiogenic activity of a stromal tissue culture by incorporating cells that release different levels of angiogenic factors. For example, vascular smooth muscle cells, preferably aortic smooth muscle cells, are known to produce substantially more VEGF than human dermal fibroblasts. Therefore, by utilizing aortic smooth muscle cells instead of or in addition to fibroblasts, one can culture three-dimensional stromal tissues with enhanced angiogenic activity.

Again, where the cultured cells are to be used for transplantation or implantation in vivo, it is preferable to obtain the stromal cells from the patient's own tissues. The growth of cells in the presence of the three-dimensional stromal support framework may be further enhanced by adding to the framework, or coating it with proteins (e.g., collagens, elastin fibers, reticular fibers) glycoproteins, glycosaminoglycans (e.g., heparan sulfate, chondroitin-4-sulfate, chondroitin-6-sulfate, dermatan sulfate, keratan sulfate, etc.), a cellular matrix, and/or other materials.

After inoculation of the stromal cells, the three-dimensional framework should be incubated in an appropriate nutrient medium. Many commercially available media such as RPMI 1640, Fisher's, Iscove's, McCoy's, and the like may be suitable for use. It is important that the three-dimensional stromal tissue be suspended in the medium during the incubation period in order to maximize proliferative activity. In addition, the culture should be "fed" periodically to remove the spent media, depopulate released cells, and add fresh media. During the incubation period, the stromal cells will grow linearly along and envelop the filaments of the three-dimensional framework before beginning to grow into the openings of the framework.

The openings of the framework should be of an appropriate size to allow the stromal cells to stretch across the openings. Maintaining actively growing stromal cells which stretch across the framework enhances the production of growth factors which are elaborated by the stromal cells, and hence will support long term cultures. For example, if the openings are too small, the stromal cells may rapidly achieve confluence but be unable to easily exit from the mesh; trapped cells may exhibit contact inhibition and cease production of the appropriate factors necessary to support proliferation and maintain long term cultures. If the openings are too large, the stromal cells may be unable to stretch across the opening; this will also decrease stromal cell production of the appropriate factors necessary to support proliferation and maintain long term cultures. When using a mesh type of framework, as exemplified herein, it has been found that openings ranging from about 140 µm to about 220 µm will work satisfactorily. However, depending upon the three-dimensional structure and intricacy of the framework, other sizes may work equally well. In fact, any shape or structure that allows the stromal cells to stretch and continue to replicate and grow for lengthy time periods will work in accordance with the invention.

Different proportions of the various types of collagen deposited on the framework can affect the growth of the cells that come in contact with the three dimensional stromal tissue. The proportions of extracellular matrix (ECM) proteins deposited can be manipulated or enhanced by selecting fibroblasts which elaborate the appropriate collagen type. This can be accomplished using monoclonal antibodies of an appropriate isotype or subclass that is capable of activating complement, and which define particular collagen types. These antibodies and complement can be used to negatively select the fibroblasts which express the desired collagen type. Alternatively, the stroma used to inoculate the framework can be a mixture of cells which synthesize the appropriate collagen types desired. The distribution and origins of the various types of collagen is shown in Table I.

TABLE I

DISTRIBUTIONS AND ORIGINS OF
VARIOUS TYPES OF COLLAGEN

| Collagen Type | Principal Tissue Distribution | Cells of Origin |
| --- | --- | --- |
| I | Loose and dense ordinary connective tissue; collagen fibers | Fibroblasts and, reticular cells; smooth muscle cells |
| | Fibrocartilage | |
| | Bone | Osteoblast |
| | Dentin | Odontoblasts |
| II | Hyaline and elastic cartilage | Chondrocytes |
| | Vitreous body of eye | Retinal cells |
| III | Loose connective tissue; reticular fibers | Fibroblasts and reticular cells |
| | Papillary layer of dermis | |
| | Blood vessels | Smooth muscle cells; endothelial cells |
| IV | Basement membranes | Epithelial and endothelial cells |
| | Lens capsule of eye | Lens fibers |
| V | Fetal membranes; placenta | Fibroblast |
| | Basement membranes | |
| | Bone | |
| | Smooth muscle | Smooth muscle cells |
| VI | Connective tissue | Fibroblasts |
| VII | Epithelial basement membranes, anchoring fibrils | Fibroblasts, keratinocytes |
| VIII | Cornea | Corneal fibroblasts |
| IX | Cartilage | |
| X | Hypertrophic cartilage | |
| XI | Cartilage | |
| XII | Papillary dermis | Fibroblasts |
| XIV, undulin | Reticular dermis | Fibroblasts |
| XVII | P170 bullous pemphigoid antigen | Keratinocytes |

Thus, since the three-dimensional culture system described herein is suitable for the growth of diverse cell types and tissues, and depending upon the tissue to be cultured and the collagen types desired, the appropriate stromal cell(s) may be selected to inoculate the three-dimensional framework.

During incubation of the three-dimensional stromal support, proliferating cells may be released from the framework. These released cells may stick to the walls of the culture vessel where they may continue to proliferate and form a confluent monolayer. This should be prevented or minimized, for example, by removal of the released cells during feeding, or by transferring the three-dimensional stromal tissue to a new culture vessel. The presence of a confluent monolayer in the vessel may "shut down" the growth of cells in the three-dimensional culture. Removal of the confluent monolayer or transfer of the stromal tissue to fresh media in a new vessel will restore proliferative activity of the three-dimensional culture system. Such removal or transfers should be done in any culture vessel which has a stromal monolayer exceeding 25% confluency. Alternatively, the culture system could be agitated to prevent the released cells from sticking, or instead of periodically feeding the cultures, the culture system could be set up so that fresh media continuously flows through the system. The flow rate could be adjusted to both maximize proliferation within the three-dimensional culture, and to wash out and remove cells released from the culture, so that they will not stick to the walls of the vessel and grow to confluence. In any case, the released stromal cells can be collected and cryopreserved for future use.

5.2 Preparation of a Genetically Engineered Three-Dimension Stromal Tissue

Genetically engineered three-dimensional stromal tissue may be prepared as described in U.S. Pat. No. 5,785,964 which is incorporated herein by reference. A genetically-engineered stromal tissue may serve as a gene delivery vehicle for sustained release of angiogenic factors in vivo.

Stromal cells may be engineered to express an exogenous gene product. Stromal cells that can be genetically engineered include, but are not limited to, fibroblasts, smooth muscle cells, cardiac muscle cells, mesenchymal stem cells, and other cells found in loose connective tissue such as endothelial cells, macrophages, monocytes, adipocytes, pericytes, reticular cells found in bone marrow, etc.

The cells and tissues may be engineered to express a target gene product which may impart a wide variety of functions, including, but not limited to, enhanced function of the genetically engineered cells and tissues to promote angiogenesis when implanted in viva. The target gene product may be a peptide or protein, such as an enzyme, hormone, cytokine, a regulatory protein, such as a transcription factor or DNA binding protein, a structural protein, such as a cell surface protein, or the target gene product may be a nucleic acid such as a ribosome or antisense molecule.

In a preferred embodiment, the target gene products which provide enhanced properties to the genetically engineered cells, include but are not limited to, gene products which enhance cell growth, e.g., vascular endothelial growth factor (VEGF), hepatocyte growth factor (HGF), fibroblast growth factors (FGF), platelet derived growth factor (PDGF), epidermal growth factor (EGF), and transforming growth factor (TGF). In another preferred embodiment, the cells and tissues are genetically engineered to express target gene products which result in cell immortalization, e.g. oncogenes or telomerese. In yet another embodiment, the cells may be engineered to express a suicide gene product on cue, e.g., thymidine kinase.

In another preferred embodiment, the cells and tissues are genetically engineered to express gene products which provide protective functions in vitro such as cyropreservation and anti-desiccation properties, e.g., trehalose (U.S. Pat. Nos. 4,891,319; 5,290,765; 5,693,788). The cells and tissues of the present invention may also be engineered to express gene products which provide a protective function in vivo, such as those which would protect the cells from an inflammatory response and protect against rejection by the host's immune system, such as HLA epitopes, major histocompatibility epitopes, immunoglobulin and receptor epitopes, epitopes of cellular adhesion molecules, cytokines and chemokines.

There are a number of ways that the target gene products may be engineered to be expressed by the cells and tissues of the present invention. The target gene products may be engineered to be expressed constitutively or in a tissue-specific or stimuli-specific manner. In accordance with this aspect of the invention, the nucleotide sequences encoding the target gene products may be operably linked to promoter elements which are constitutively active, tissue-specific or induced upon presence of a specific stimuli.

In a specific embodiment, the nucleotide sequences encoding the target gene products are operably linked to regulatory promoter elements that are responsive to shear or radial stress. In this instance, the promoter element would be turned on by passing blood flow (shear) as well as the radial stress that is induced as a result of the pulsatile flow of blood through the heart or vessel.

Examples of other regulatory promoter elements include tetracycline responsive elements, nicotine responsive elements, insulin responsive element, glucose responsive elements, interferon responsive elements, glucocorticoid responsive elements estrogen/progesterone responsive elements, retinoid acid responsive elements, viral transactivators, early or late promoter of SV40 adenovirus, the lac system, the trp system, the TAC system, the TRC system, the promoter for 3-phosphoglycerate and the promoters of acid phosphatase. In addition, artificial response elements could be constructed, composed of multimers of transcription factor binding sites and hormone-response elements similar to the molecular architecture of naturally-occurring promoters and enhancers (e.g., see Herr, W & Clarke, J Cell (1986) 45(3): 461-70). Such artificial composite regulatory regions could be designed to respond to any desirable signal and be expressed in particular cell-types depending on the promoter/enhancer binding sites selected.

5.3 Uses of a Three-Dimensional Stromal Tissue in Promoting Angiogenesis

The three-dimensional stromal tissue of the present invention may be used in a variety of applications including, but not limited to, promoting repair of and regeneration of damaged cardiac muscle, promoting vascularization and healing during cardiac surgery (e.g. by-pass surgery or heart valve replacement), promoting blood vessel formation at anastomosis sites, and promoting vascularization and repair of ischemic or otherwise damaged smooth muscle, cardiac muscle, skeletal muscle, connective tissue or brain tissue. In that connection, stromal tissue may be used as a freshly cultured tissue, as a cryopreserved tissue, or even as a killed tissue.

The three-dimensional stromal tissue of the present invention may be attached to various locations on the heart, including the eipcardium, myocardium and endocardium, to promote angiogenesis in the region of attachment. Means for attachment include, but are not limited to, direct adherence between the stromal tissue and the heart tissue, biological glue, synthetic glue, laser dyes, or hydrogel. A number of commercially available hemostatic agents and sealants include "SURGICAL" (oxidized cellulose), "ACTIFOAM" (collagen), "FIBRX" (light-activated fibrin sealant), "BOHEAL" (fibrin sealant), "FIBROCAPS" (dry powder fibrin sealant), polysaccharide polymers p-GlcNAc ("SYVEC" patch; Marine Polymer Technologies), Polymer 27CK (Protein Polymer Tech.). Medical devices and apparatus for preparing autologous fibrin sealants from 120 ml of a patient's blood in the operating room in one and one-half hour are also known (e.g. Vivostat System).

In an embodiment of the invention utilizing direct adherence, the three-dimensional stromal tissue is placed directly onto the heart or an adjoining vessel and the product attaches via natural cellular attachment. This method has been demonstrated in studies of wound healing in patients with diabetic foot ulcers.

In a preferred embodiment, a three-dimensional stromal tissue is attached to the heart or adjoining vessel using a surgical glue, preferably a biological glue such as a fibrin glue. The use of fibrin glue as a surgical adhesive is well known. Fibrin glue compositions are known (e.g., see U.S. Pat. Nos. 4,414,971; 4,627,879 and 5,290,552) and the derived fibrin may be autologous (e.g., see U.S. Pat. No. 5,643,192). The glue compositions may also include additional components, such as liposomes containing one or more agent or drug (e.g., see U.S. Pat. Nos. 4,359,049 and 5,605,541) and include via injection (e.g., see U.S. Pat. No. 4,874,368) or by spraying (e.g., see U.S. Pat. Nos. 5,368,563 and 5,759,171). Kits are also available for applying fibrin glue compositions (e.g., see U.S. Pat. No. 5,318,524).

In another embodiment, a laser dye is applied to the heart and/or vessel wall, the three-dimensional stromal tissue, or both, and activated using a laser of the appropriate wavelength to adhere to the tissues. In preferred embodiments, the laser dye has an activation frequency in a range that does not alter tissue function or integrity. For instance, 800 nm light passes through tissues and red blood cells. Using indocyan green (ICG) as the laser dye, laser wavelengths that pass through tissue may be used. A solution of 5 mg/ml of ICG is painted onto the surface of the three-dimensional stromal tissue (or target site) and the ICG binds to the collagen of the tissue. A 5 ms pulse from a laser emitting light with a peak intensity near 800 nm is used to activate the laser dye, resulting in the denaturation of collagen which fuses elastin of the adjacent tissue to the modified surface.

In another embodiment, the three-dimensional stromal tissue is attached to the heart or vessel using a hydrogel. A number of natural and synthetic polymeric materials are sufficient for forming suitable hydrogel compositions. For example, polysaccharides, e.g., alginate, may be crosslinked with divalent cations, polyphosphazenes and polyacrylates are crosslinked ionically or by ultraviolet polymerization (U.S. Pat. No. 5,709,854). Alternatively, a synthetic surgical glue such as 2-octyl cyanoacrylate ("DERMABOND", Ethicon, Inc., Somerville, N.J.) may be used to attach the three-dimensional stromal tissue.

In an alternative embodiment of the present invention, the three-dimensional stromal tissue is secured to the heart or a blood vessel vessels using one or more sutures, including, but not limited to, 5-O, 6-O and 7-O proline sutures (Ethicon Cat. Nos. 8713H, 8714H and 8701H), poliglecaprone, polydioxanone, polyglactin or other suitable non-biodegradable or biodegradable suture material. When suturing, double armed needles are typically, although not necessarily, used.

In another embodiment, the three-dimensional stromal tissue is grown in a bioreactor system (e.g., U.S. Pat. Nos. 5,763,267 and 5,843,766) in which the framework is slightly larger than the final tissue-engineered product. The final product contains a border, one edge, flap or tab of the scaffold material, which is used as the site for application of the biological/synthetic glue, laser dye or hydrogel. In alternative embodiments, the scaffold weave may be used as an attachment for suturing or microsuturing.

The three-dimensional stromal tissue may be implanted to promote vascularization, repair and regeneration of damaged cardiac muscle. In a preferred embodiment, the three-dimensional stromal tissues will be applied to a vessel to sprout new blood vessels to by-pass clogged or blocked arteries and restore blood flow to the heart. In another embodiment, the three-dimensional stromal tissue will be applied directly to the heart using a minimally invasive procedure. The tissue can be applied to promote vascularization and blood flow to minimize necrosis and/or promote regeneration of heart tissue following a myocardial infarction. When attaching a three-dimensional stromal tissue to the heart epicardium or myocardium, it will be necessary to open the pericardium (i.e., the heart sac) prior to application. However, attaching a three-dimensional stromal tissue patch to the endocardium may be accomplished by inserting a catheter or similar device into a ventricle of the heart and adhering or attaching the stromal patch to the wall of the ventricle. It is preferred that the site of attachment should have a reasonably good blood flow to support angiogenesis.

The angiogenic activity of the three-dimensional stromal tissues may also be used for treating anastomoses. An anastomosis is defined as an operative union between two hollow or tubular structures or an opening created by surgery, trauma or disease between two or more separate spaces or organs (see, e.g., Stedman's Medical Dictionary, $26^{th}$ Ed, Williams & Wilkins, Baltimore, Md.). For instance, anastomotic sites arise from the introduction of a vascular graft during a coronary artery bypass graft (CABG) procedure, during a bowel resection or organ transplant. In CABG procedures, a three-dimensional tissue is placed at the site of downstream attachment of the bypass graft to promote angiogenesis upon restoration of blood flow to that site, i.e. to form additional arteries arising from the connection sites in addition to promoting healing of the site. Examples in the vascular field include, but are not limited to, precapillary (between arterioles), Riolan's (marginal artery of the colon connecting the middle and left colic arteries), portal-systemic (superior-middle/inferior rectal veins; portal vein-inferior vena cava), termino-terminal (artery to vein) and cavo-pulmonary (treating cyanotic heart disease by anastomosing the right pulmonary artery to the superior vena cava).

In one embodiment, the three-dimensional stromal tissue is wrapped around the anastomotic site to promote healing of the site (i.e., endothelialization). In another embodiment, the cells of the three-dimensional stromal tissue are killed (e.g., by freezing and thawing) and the resulting product is applied to the site (i.e., "TRANSCYTE").

As described above, encompassed within the scope of the invention is a method for treating ischemic damage in tissues including, but not limited to, heart, brain peripheral tissues and visceral organs. A three-dimensional stromal tissue implant is attached to the ischemic site using natural adherence, a suture, adhesive or other means as described above. The implanted three-dimensional stromal tissue promotes formation of new blood vessels and healing of the damaged tissue.

Also encompassed within the scope of the invention is a kit for promoting angiogenesis comprising a three-dimensional stromal tissue and a means for attaching such tissue to the heart or vessels. Such means for attachment include a composition of surgical glue, hydrogel, preloaded prolene needles for microsuturing.

6. EXAMPLE

Three-Dimensional Stromal Tissue Promoted Angiogenesis

This section demonstrates that a fibroblast-based three-dimensional stromal tissue ("stromal tissue") was capable of inducing endothelialization and vascularization. Providing such a biologically active material has been observed to induce new capillary formation and reduce inflammation in the wound bed of patients with diabetic foot ulcers.

The angiogenic properties of three-dimensional stromal tissues are described below using a wide range of techniques including the chick chorioallantoic membrane assay, the rat aortic ring assay, stimulation of endothelial cell proliferation, chemokinesis, chemotaxis, inhibition of apoptosis, and in vivo induction of angiogenesis in ischemic heart tissue. Collectively, these assays cover a wide range of the individual events in angiogenesis as well as the overall process.

The fibronectin present in the extracellular matrix also has been shown to stimulate the proliferation of endothelial cells, while the denatured collagen has been proven to be a favorable substrate for human endothelial cell attachment. Bound growth factors in the matrix include TGFβ and HGF which are important in stimulating new capillary formation and endothelialization. The matrix also contains laminin-1 which can serve to inhibit initial hyperplasia via the YIGSR peptide. The combination of these matrix proteins along with naturally secreted growth factors offers a physiological solution to the in vivo induction of angiogenesis.

6.1 Materials and Methods

6.1.1. Expression of Growth Factors by Three-Dimensional Stromal Tissue

Experiments were performed to examine the expression of angiogenic factors by the stromal tissues. Growth factor expression was examined both by estimation of mRNA by polymerase chain reaction (PCR) methods and estimation of the free protein by enzyme-linked immunosorption assay (ELISA).

Specific messenger RNAs were estimated by quantitative RT-PCR using the ABI TaqMan method (Perkin-Elmer, Foster City, Calif.). RNA was extracted from the cells using a Rapid RNA Purification Kit (Amresco, Solon, Ohio). The RNA was reverse transcribed using Superscript II (Life Technologies, Grand Island, N.Y.) with random hexamer primers (Sigma, St. Louis, Mo.). Amplification of samples of cDNA containing 200 ng total RNA was detected in real time and compared with the amplification of plasmid-derived standards for specific mRNA sequences using a copy number over a range of 5 orders of magnitude with 40-4,000,000/reaction. In purification and the efficiency of reverse transcription, mRNA sequences for PDGF B chain, VEGF or TGFβ1 were added to RNA isolations, and their yield measured by the TaqMan procedure. The control mRNA sequences were obtained by T7 RNA polymerase transcription of plasmids containing the corresponding sequence. The values were normalized using glyceraldehyde-3-phosphate dehydrogenase as a control.

6.1.2. Chick Chorioallantoic Membrane Assay

Ten day old chicken embryos were obtained from McIntyre Farms (Lake, Calif.) and incubated at 37° C. Eggs were candled to locate and mark a target area void of large vessels. Two small holes were made in the shell with a needle, directly over the air sac and over the target area. Suction was applied to the first hole, causing the CAM to drop away from the marked area. Using a "DREMEL MOTO-TOOL", the egg shell was removed from the target area to create a "window." A 4 mm diameter circular sample (three-dimensional stromal tissue or control) was then placed on the membrane near, but not on top of, a large blood vessel. The hole was covered with a piece of clear adhesive tape and the eggs were incubated for 72 hours at 37° C. to allow blood vessel growth. The treated section of the membrane was then removed, photographed, and fixed in methanol. The number of fine blood vessel branch points in the region of the sample was counted. Biopsy samples were fixed in methanol and sections stained with Masson's Trichrome.

6.1.3. Aortic Ring Assay

In the aortic ring assay, the ability of the endothelial blood vessel lining to generate microvessels was used to demonstrate angiogenesis. Thoracic aortas removed from 1 to 2 month old Sprague Dawley male rats were transferred to serum-free MCDB131. The peri-aortic fibroadipose tissue was carefully removed, the aortas washed 8 to 10 times and cut into 1 mm lengths. Wells were punched in a 1.5% agarose gel and filled with clotting fibrinogen solution (20 μL 50 NIH units/mL bovine thrombin in 1 mL fibrinogen). The aortic rings were placed into the centers of the wells. After clotting, the dishes were flooded with serum-free MCDB131. The cultures were incubated at 37° C. with 5% $CO_2$, with medium changes every 3 days. Newly formed microvessels were counted on days 3, 7 and 14.

6.1.4. Endothelial Cell Proliferation Assay

Endothelial cell proliferation is a critical component of angiogenesis. The ability of the stromal tissue to stimulate this activity was determined by [$^3$H]-thymidine incorporation. Various growth factors and concentrated conditioned medium samples were assessed for their influence on the proliferation of HUVEC. Confluent cultures were detached and re-suspended in HUVEC growth medium to a final concentration of $2.5 \times 10^4$ cells/ml. 24-well plates were pre-treated with Attachment Factor Solution (Cell Applications, Inc.) and cells were added at 1 ml cell suspension per well. Cells were allowed to settle and attach, and then were switched to Endothelial Serum Free Medium (Cell Applications, Inc.), supplemented with fibroblast culture medium or medium conditioned by monolayer or three-dimensional fibroblast cultures. On day two, the cells received fresh serum free medium supplemented as appropriate with 1 μCurie/ml [$^3$H]-thymidine. On day three, medium was removed, cells were washed three times with PBS, and 250 μl 2.3% sodium dodecyl sulfate (SDS) was added to solubilize the cells. After 30 minutes; the SDS extract and one ml of a PBS wash were transferred to a scintillation vial. Five ml of "SCINTI-VERSE" (Fair Lawn, N.J.) was added to vials and radioactivity was determined using a Beckman LS6500 Scintillation Counter (Fullerton, Calif.).

6.1.5. Endothelial Cell Chemokinesis Assay

The ability of our three-dimensional stromal tissue to stimulate endothelial cell migration was tested in two ways. The first was a chemokinesis assay that determined the stimulation of cell movement without any directional definition. The second measured cell migration towards a stimulation source.

Endothelial cells were grown on Cytodex-2 beads. The assay estimated the dissociation of cells from the beads and re-association with a culture plate. The cells on the plate were stained and counted.

6.1.6. Endothelial Cell Chemotaxis Assay

Cell migration was analyzed with an endothelial cell chemotaxis assay utilizing a Neuro Probe 48-well Boyden chemotaxis chamber (Neuro Probe, Inc.). Polycarbate membrane filters (Poretics Corporation, 25×80 mm) were soaked in 0.5M acetic acid overnight, washed three times for 1 hour with water, incubated in a solution of 0.01% calf skin gelatin type III, (Sigma, St. Louis, Mo.) for 12-16 hours, and air dried. HUVECs were detached and resuspended in HUVEC growth medium at a final concentration of $1.0 \times 10^5$ cells/ml. The Boyden Chamber was assembled as follows: 30 μl of sample or standard was added to the bottom wells, the gelatin coated membrane was placed on top, and 50 μl cell suspension was added to the upper wells. The chamber was incubated at 37° C. for 3 hours. Membranes were then carefully removed from the chamber and the cell-side was rinsed in PBS and drawn across a wiper blade to remove non-migrated cells. The membranes were stained with Wright's Giemsa stain and either the number of cells counted or the density of staining was reported against a standard curve generated with 20, 10, 5.0 and 0 ng/ml purified VEGF.

6.1.7. Induction of Integrin

The αvβ3 integrin has been shown to play an important role in angiogenesis and neutralizing antibodies directed at it are capable of blocking capillary blood vessel formation. It is induced by VEGF and is thought to play a critical role in the endothelial cell migration.

The presence of integrins and cell surface receptors was determined by flow cytometry on a FACStar by Cytometry Research Services, San Diego, Calif. Cells were prepared for analysis as follows: HUVECs were trypsinized and the cells re-suspended at $1 \times 10^6$ cells/ml. 250 μL to 500 μL of the cell suspensions were washed three times with Hank's Balanced Salt Solution (HBSS, GibcoBRL, Grand Island, N.Y.), and finally re-suspended in 10% FBS in Hank's balanced salt solution (HBSS). The cells were incubated for 30 minutes with primary antibodies diluted to 1 μg/ml in 10% FBS in HBSS, washed three times with HBSS, incubated for 30 minutes with secondary antibodies diluted to 1 μg/mL in 10% FBS in HBSS, washed three times with HBSS, and fixed in 200 μL 10% Formalin (Baxter, Deerfield, Ill.) at a density of $10^6$ cells/mL.

6.1.8. Inhibition of Endothelial Cell Apoptosis

It has been previously reported that endothelial cells cultured as a monolayer on "MATRIGEL", a basement membrane growth substrate (Collaborative Research) coalesced into tubes and underwent apoptosis. The inclusion of an angiogenic factor, e.g., VEGF in the "MATRIGEL", however, maintained endothelial cell proliferation and morphology suggesting that the angiogenic activity of VEGF inhibited apoptosis (e.g., see Goto et al., 1993, Lab Invest. 69:508-517; and Haralbopoulos et al., 1994, Lab Invest. 71:575-582).

To further evidence the angiogenic activity of the three-dimensional stromal tissues of the present invention, growth medium conditioned by a three-dimensional stromal tissue was added to endothelial cells cultured on "MATRIGEL" to demonstrate the inhibiiton of apoptosis. "MATRIGEL" was thawed and solidified in "TRANSWELL" (Costar, Boston, Mass.) 6-well tissue culture dishes according to the manufacturer's instructions. Dermal microvascular endothelial cells (DMEC) were seeded onto the solidified "MATRIGEL" at $2.5 \times 10^5$ cells/well, in the presence of growth medium conditioned by a monolayer culture of fibroblasts or three-dimensional fibroblast culture, and incubated at 37° C. in a 5% $CO_2$ atmosphere as previously described (e.g., see Kuzuya et al., 1994, J. Cell Physiol. 161:267-276). The DMEC cells of each culture were stained by incubating the culture in a solution of 10 μg/ml di-1-acetyl-low density lipoprotein for 2-4 hours (e.g., see Voyta et al., 1984, J. Cell Biol. 99:2034-2040) and a solution of "SYTOX", which stained cell nuclei (Molecular Probes, Eugene, Oreg.).

6.1.9. Blood Flow Changes in Human Diabetic Foot Ulcers

Cultured three-dimensional stromal tissue provides many of the components of healthy skin essential for wound healing, including important mediators of angiogenesis like VEFG and transforming growth factor-β (TGFβ). Laser Doppler imaging was used to study microvascular perfusion at the base of foot ulcers treated with three-dimensional stromal tissue, to investigate whether healing of these lesions was associated with an increase in blood flow that might in turn reflect angiogenesis.

Seven full-thickness ulcers were assessed in five patients with type 2 diabetes mellitus. All lesions had been present for at least three months with no clinical evidence of infection or change in size over the previous two weeks, despite conventional treatment. Three-dimensional stromal tissue was applied weekly to the base of each wound for a total of eight weeks, after which conventional treatment was resumed. Microvascular perfusion was assessed using laser Doppler imaging (Moore Instruments, Axminster, UK) immediately before and after 2, 5 and 8 weeks of treatment.

6.1.10. Stimulation of Vascularization in a Mouse Epicardial Implant Model 6.1.10.1. Animals Three-dimensional stromal tissue-stimulated vascularization was examined in vivo using a Severe Combined Immunodeficiency (SCID) mouse epicardial implant model. Mice were divided into three groups: viable/cryopreserved three-dimensional stromal tissue implant ("viable stromal patch"), non-viable three-dimensional stromal tissue implant ("non-viable stromal patch"), and control/sham. Each group had at least six animals per group at two separate time points (14 days and 30 days). The animal study was performed in accordance with applicable regulations of the United States Food and Drug Administration.

6.1.10.2. Animal Husbandry

SCID mice (University of Arizona, Tucson, Ariz.) were housed 2 per cage in micro-isolator cages on wood shavings and received "TECH-LAD 4% MOUSE/RAT DIET" and tap water ad libitum. Mice were housed under controlled temperatures of 74° F.±10° F. and humidity 50%±20% in accordance with the NIH "Guide for the Care and Use of Laboratory Animals".

6.1.10.3. Surgical Procedures

General anesthesia was induced and maintained by an intraperitoneal injection of 2.5% Avertin. Sterility was maintained and a warming pad was used throughout the procedure. Mice were weighed, and the chest wall shaved and prepared. In the supine position, a tracheotomy was performed, and mice ventilated using a small animal respirator (tidal volume=0.5 ml, rate=120-130 breaths/min). Proper intubation was confirmed by observation of chest expansion and retraction during ventilated breaths.

All surgical procedures were carried out using an operating microscope. A left thoracotomy was performed and the pectoralis muscle groups were cut transversely, exposing the thoracic cage. The fourth intercostal space was entered using scissors and blunt dissection. Two 6-0 silk sutures (Ethicon) were placed around the upper and lower ribs for retraction. The thymus was retracted upward, and the left lung collapsed using a sterile cotton swab. Pressure was then applied to the right thorax to displace the heart in a leftward direction.

To induce epicardial/myocardial ischemic damage, a coronary occlusion of the left coronary artery just below the left atrium was performed by thermal occlusion using standard methods known to those of skill in the art. Occlusion results in an area of non-viable, ischemic tissue located primarily in the left ventricle near the apex. A 4 mm viable stromal patch or non-viable stromal patch was sutured onto the surface of the ischemic epicardial/myocardial tissue of surviving mice using a single suture. For control mice, only a suture was introduced at the site of ischemic damage. Following implantation, the lungs were re-expanded using positive pressure at end expiration. The chest cavity was closed in layers using 6-0 silk (Ethicon, Inc.) and the animal were gradually weaned from the respirator. Once spontaneous respiration was resumed, the tracheal tube was removed, and the neck closed. The animals remained in a supervised setting until fully conscious and the post-operative general health status of each animal was determined daily.

Prior to explant, an echocardiogram was performed to measure ventricular wall thickness and compare to that prior to occlusion. At 14 days or 30 days, mice were re-anesthetized and the three-dimensional stromal tissue patches with surrounding tissue and control heart tissues were harvested. Mice were euthanized after material harvest using an overdose (150 mg/kg) of pentobarbital IP.

6.1.10.4 Analyses

The in vivo formation of new blood vessels in stromal patch-treated animals and controls was examined using three separate analyses: gross morphology, histology and histochemistry.

The gross morphology of a representative heart from each group was examined to access the tissue viability in the ischemic region. The gross morphology of the heart was examined by injecting one explanted heart from each group with the dye tetrazolium red (2,3,5-triphenyltetrazolium chloride) (Sigma/Aldrich Chemical Co., St. Louis, Mo.). Tetrazolium red reacts with viable heart tissue producing a bright red color. In contrast, non-viable tissue does not react with tetrazolium red thus leaving non-viable tissue a pale white color. Explanted hearts from 14 day and 30 day control mice and stromal patch-treated mice exhibited a region of non-viable ischemic heart tissue located primarily in the left ventricle resulting from the induced coronary occlusion/myocardial infarction. Images taken at low and high power revealed a large area of non-viable heart tissue, as evidenced by the pale white color. In the controls, the ischemic area is devoid of visible blood vessels.

The three-dimensional stromal tissue-dependent formation of new blood vessel was confirmed by histological analysis of sections of treated and control heart tissues. For histological analysis, the stromal patch implants and adjacent tissues were excised and placed in "HISTOCHOICE" fixative (MANUFACTURER) and processed for light microscopy. The stromal tissue patches and surrounding tissues were sectioned, placed on slides and stained using hematoxylin and eosin (H & E). Histological staining using H & E is well known to those of skill in the art (e.g., In *Histology: A Text and Atlas,* 3rd ed. (Ross et al., ed), pp. 1-7; Williams and Wilkins, Baltimore, Md.) and kits and reagents are readily available from commercial suppliers (e.g., Sigma/Aldrich Chemical Co., St Louis, Mo.).

In addition, the three-dimensional stromal tissue-dependent formation of new blood vessels was verified using histochemistry to specifically identify the presence and location of vascular endothelial cells present in histological sections. The stromal patch implants and surrounding tissues were sectioned, placed on slides and histochemically stained using GS-1. GS-1 is a commercially available lectin that primarily binds to the surface of endothelial cells (Sigma/Aldrich Chemical Co.).

6.2. Results

6.2.1. Three-Dimensional Stromal Tissue Expressed Angiogenic Growth Factors Engineered three-dimensional stromal tissue secreted a variety of growth factors, some of which are known to play an important role in tissue regeneration and angiogenesis. Angiogenic growth factors expressed by fibroblast-based three-dimensional stromal tissue are shown in Table II. Cellular concentrations of mRNA were determined after 24 h recovery from thawing.

TABLE II

THREE-DIMENSIONAL STROMAL TISSUE EXPRESSED ANGIOGENIC GROWTH FACTORS

| Growth factor | Expressed, by Q-RT-PCR | Secreted, by ELISA | Potential importance in wound healing |
|---|---|---|---|
| VEGF | $8 \cdot 10^6$ copies/µg RNA | 700 pg/$10^6$ cells/day | Mainly 121 amino acid form |
| PDGF A chain | $6 \cdot 10^5$ copies/µg RNA | | Autocrine environmental sensor |
| PDGF B chain | 0 | 0 | Not made |
| IGF-1 | $5 \cdot 10^5$ copies/µg RNA | | Co-stimulator of proliferation |
| EGF | $3 \cdot 10^3$ copies/µg RNA | | Negligible |
| HBEGF | $2 \cdot 10^4$ copies/µg RNA | | |
| KGF | $7 \cdot 10^4$ copies/µg RNA | | Probably requires induction by IL-1 |
| TGFβ$_1$ | $6 \cdot 10^6$ copies/µg RNA | 300 pg/$10^6$ cells/day | Major product |
| TGFβ$_3$ | $1 \cdot 10^4$ copies/µg RNA | | Minor product |
| HGF | $2 \cdot 10^4$ copies/µg RNA | 1 ng/$10^6$ Cells/day | |
| IL-1α | $1 \cdot 10^4$ copies/µg RNA | Below detection | Very low output |
| IL-1β | 0 | | Not produced |
| TNFα | $1 \cdot 10^7$ copies/µg RNA | | Substantial expression |
| TNFβ | 0 | | Not expressed |
| IL-6 | $7 \cdot 10^6$ copies/µg RNA | 500 pg/$10^6$ cells/day | Potentially important |
| IL-8 | $1 \cdot 10^7$ copies/µg RNA | 25 ng/$10^6$ cells/day | Major product |
| IL-12 | 0 | | Not expressed |
| IL-15 | 0 | | Not expressed |
| NGF | 0 | | Not expressed |
| G-CSF | $1 \cdot 10^4$ copies/µg RNA | 300 pg/$10^6$ cells/day | Potentially important |
| Angiopoietin-1 | $1 \cdot 10^4$ copies/µg RNA | | Probably negligible |

6.2.2. Three-Dimensional Stromal Tissue Stimulated Angiogenesis in the Chick Chorioallantoic Membrane and Rat Aortas The three-dimensional FBET induced vessel development in the CAM to a greater extent as compared to control (FIG. 1A-1D), including both fine capillary development and evidence for increased permeability. The development of capillary blood vessels in CAM treated with FBET was also clearly visible by histology. This type of capillary development is characteristic of VEGF-induced angiogenesis. It differed from what was seen with basic FGF stimulation where the vessels showed a larger diameter with little or no increase in permeability. When the number of vessels per sample in the CAM was counted, there was a statistically significant difference between the effects of scaffold alone and three-dimensional FBET (FIG. 2). The angiogenic activity of the three-dimensional tissue was reduced by >90% by pre-incubation with anti-VEGF neutralizing antibody prior to placement on the CAM, indicating that VEGF production by FBET was important in its angiogenic activities. When aortic rings of rat thoracic aortas were co-cultured with FBET, there was a significant increase in the number of microvessels formed (FIG. 3). It is believed that the FBET produces a combination of angiogenic factors in naturally-secreted ratios that may have a synergistic effect.

6.2.3. Three-Dimensional Stromal Tissue Stimulated Endothelial Cell Proliferation Three-dimensional stromal tissue-conditioned medium stimulated human endothelial cell proliferation, as measured by [$^1$H]-thymidine incorporation as described in section 6.1.4 above (FIG. 4). The stimulatory activities of the medium were dose dependent.

6.2.4. Three-Dimensional Stromal Tissue Stimulated Endothelial Cell Chemokinesis As shown in FIG. 5, co-culture of endothelial cells with three-dimensional stromal tissue induced a marked increase in the transfer of cells from beads to plate (p=0.0003), which was used as an indication of chemokinesis. This stimulating activity of the three-dimensional stromal tissue was inhibited about 60% by anti-hepatocyte growth factor (HGF) neutralizing antibody, indicating that HGF was also involved.

6.2.5. Three-Dimensional Stromal Tissue Stimulated Endothelial Cell Chemotaxis Medium conditioned with three-dimensional stromal tissue also stimulated cell migration in a dose-dependent manner (FIG. 6). In fact, the stromal tissue stimulated greater chemotaxis as compared with VEGF, even at 50 ng/L. Anti-VEGF antibody inhibited cell migration stimulated by stromal tissue conditioned medium by 50%.

6.2.6. Three-Dimensional Stromal Tissue Induced Integrin αvβ3 Expression

The presence of αvβ3 integrin on the surface of endothelial cells was analyzed by flow cytometry after treatment with medium conditioned by three-dimensional stromal tissue. Cultured HUVECs displayed substantial surface expression of αvβ3 integrin under normal culture conditions. However, medium conditioned by stromal tissue stimulated a significant increase in expression of this integrin (FIG. 7).

6.2.7. Three-Dimensional Stromal Tissue Inhibited Apoptosis of Human Dermal Microvascular Cells Human dermal microvascular cells, when placed under certain specific conditions such as in a collagen gel overlay or on "MATRIGEL", form tubules. The tubules are, however, unstable and degenerate by apoptosis of the cells within about 3 days. However, if co-cultured with three-dimensional stromal tissue, microvascular endothelial cells on "MATRIGEL" continued to proliferate and apoptosis was inhibited (FIGS. 8A and 8B).

The conditioned medium obtained from monolayer culture dermal fibroblasts showed no inhibition of apoptosis with the cells forming tubules and undergoing apoptosis (FIG. 8A). In contrast, the conditioned medium obtained from three-dimensional fibroblast cultures maintained cellular proliferation and morphology similar to that observed for angiogenic factors such as bFGF and VEGF (FIG. 8B). The results demonstrate two features: 1) the conditioned medium of three-dimensional cultures was capable of inhibiting cellular apoptosis in the "MATRIGEL" assay similar to addition of angiogenic factors; three-dimensional stromal tissue produced and secreted VEGF and HGF; and, thus the inhibition of apoptosis is presumed to be the result of the angiogenic factors secreted into the medium; and 2) the same fibroblasts grown in monolayer did not produce such an effect demonstrating that the three-dimensional culture conditions were responsible for the activity (i.e. angiogenic factor expression/secretion was nonexistent or greatly diminished with a monolayer of fibroblasts).

6.2.7. Three-Dimensional Stromal Tissue Stimulated Vascularization and Increased Blood Flow in Human Diabetic Foot Ulcers Blood flow at the base of diabetic foot ulcers treated with three-dimensional stromal tissue increased significantly over the eight weeks of treatment, from 325+184 (mean+SD) to a peak of 560+344 arbitrary perfusion units (p<0.001, repeated measures ANOVA). Five of the lesions had healed by twelve weeks and the other two had markedly reduced in size. These changes in blood flow indicate angiogenesis in the newly forming granulation tissue, enhanced by a sustained and appropriate supply of angiogenic growth factors provided by the three-dimensional stromal tissue.

Similarly, photomicrographs taken before and after treatment with stromal tissue showed rapid vascularization of the wound bed, remodeling of the wounded tissue, and reduction in inflamation following treatment (FIGS. 9A-9D).

6.2.8. Three-Dimensional Stromal Tissue Stimulated Vascularization in Ischemic Heart Tissue The in vivo formation of new blood vessels in stromal patch treated mice and controls was examined using three types of analyses (gross morphology, histology and histochemistry) as described in section 6.1.10 above.

6.2.8.1 Gross Morphology and Pathology Results

With respect to the implanted animals, data obtained from 14 and 30 day stromal patch implanted hearts demonstrated that viable and non-viable stromal patch implants were well incorporated into the native heart tissue at the site of implantation. Moreover, the application of a viable stromal patch at the ischemic site resulted in the visually observable formation of a number of new blood vessels in the ischemic area that was not observed in untreated control animals. For instance, images taken under magnification clearly demonstrate the presence of numerous blood vessels in the area of implantation using a viable stromal patch implant. New blood vessel formation at the area of implantation was also observed in the non-viable stromal patch hearts. The number of new blood vessels formed, however, appeared to be appreciably greater in the viable stromal patch treated mice than non-viable stromal patch treated animals.

The gross morphological observations demonstrate that a three-dimensional stromal tissue of the instant invention is capable of promoting angiogenesis in heart tissue.

6.2.8.2 Histology Results

Light micrographs of sections obtained from normal, untreated SCID mouse hearts illustrate the organization of the myocardium and the outer most portion of the heart's surface, the epicardium. The myocardial layer contains arterioles, capillaries and venules. Compared to normal SCID mice, the induction of myocardial infarction by coronary occlusion resulted in a dramatic decrease in the number of detectable venules present in the epicardial layer.

In contrast, light micrographs of sections obtained from stromal patch treated hearts showed numerous new vessels formed in the epicardial layer and the presence of arterioles located in the myocardium near the epicardial/myocardial interface. Similarly, non-viable stromal patch treated animals showed the presence of new vessel formation in the epicardial layer but to a much lesser degree than viable stromal patch treated hearts. The histological results confirm the gross morphological observations that the three-dimensional stromal tissues of the instant invention promote new, blood vessel formation.

6.2.8.3 Histochemistry Results

Light micrographs of sections of stromal patch treated hearts revealed the presence of vascular endothelial cells lining vessels in the epicardium as well as venules and arterioles in myocardium. A reduced number of microvascularization was detected in non-viable stromal patch treated hearts. In contrast, little staining was observed of endothelial lined vessels in the epicardium of control hearts. These results demonstrate that three-dimensional stromal tissues of the instant invention stimulate angiogenesis in vivo.

The present invention is not to be limited in scope by the exemplified embodiments, which are intended as illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for effecting angiogenesis in ischemic heart tissue of a subject, comprising:
    contacting ischemic heart tissue of said subject with a three-dimensional stromal tissue,
    wherein said three-dimensional stromal tissue comprises fibroblasts and connective tissue proteins naturally secreted by the fibroblasts, said fibroblasts being attached to and substantially enveloping a framework composed of a biocompatible, non-living material formed into a three-dimensional structure having interstitial spaces bridged by the fibroblasts;
    wherein fibroblasts are the sole cell type present in the three-dimensional stromal tissue, and
    wherein said stromal tissue is capable of effecting angiogenesis in ischemic heart tissue.

2. The method of claim 1 wherein the framework is composed of a biodegradable material.

3. The method of claim 2 wherein the biodegradable material is polyglycolic acid, catgut sutures, cellulose, gelatin, collagen, or dextran.

4. The method of claim 1 wherein the framework is a mesh.

5. The method of claim 1 wherein the stromal tissue is obtained directly from a fresh culture.

6. The method of claim 1 wherein the stromal tissue has been cryopreserved.

7. The method of claim 1 further comprising adhering the stromal tissue to the ischemic heart tissue by natural cellular attachment.

8. The method of claim 1 further comprising attaching the stromal tissue to the ischemic heart tissue by means of a biodegradable or non-biodegradable suture, a biologic glue, a synthetic glue, a laser dye, or a hydrogel.

9. The method of claim 1 wherein the ischemic tissue is of the heart epicardium.

10. A method for effecting vascularization in damaged cardiac tissue of a subject, comprising
    attaching a three-dimensional stromal tissue to an epicardial or myocardial surface near a damaged region of cardiac tissue of a subject,
    wherein the three-dimensional stromal tissue comprises fibroblasts and connective tissue proteins naturally secreted by the fibroblasts, said fibroblasts being attached to and substantially enveloping a framework composed of a biocompatible, non-living material formed into a three-dimensional structure having interstitial spaces bridged by the fibroblasts;
    wherein fibroblasts are the sole cell type present in the three-dimensional stromal tissue, and
    wherein said stromal tissue is capable of effecting vascularization in damaged cardiac tissue.

11. The method of claim 10, wherein the damaged region is ischemic.

12. The method of claim 10, wherein said attaching comprises attaching the stromal tissue to the damaged region by means of a biodegradable or non-biodegradable suture, a biologic glue, a synthetic glue, a laser dye, or a hydrogel.

* * * * *